United States Patent [19]
McFadden et al.

[11] Patent Number: 5,225,324
[45] Date of Patent: Jul. 6, 1993

[54] DIAGNOSTICS FOR MYCOBACTERIA IN PUBLIC HEALTH, MEDICAL, AND VETERINARY PRACTICE

[75] Inventors: John-Jo McFadden; John Hermon-Taylor, both of London, England

[73] Assignee: Bioscience International, Inc., Boston, Mass.

[21] Appl. No.: 869,886

[22] Filed: Apr. 14, 1992

Related U.S. Application Data

[63] Continuation of Ser. No. 185,113, Apr. 22, 1988, abandoned.

[30] Foreign Application Priority Data

Apr. 24, 1987 [GB] United Kingdom ............... 8709803

[51] Int. Cl.$^5$ .................. C12Q 1/68; C12Q 1/02; G01N 33/566; C07H 15/12
[52] U.S. Cl. .................................. 435/6; 435/29; 435/34; 435/91; 436/501; 436/94; 935/77; 935/78; 536/23.1; 536/23.7
[58] Field of Search .................. 435/6, 863-866, 435/320; 436/501, 94; 536/28, 27, 26, 29; 935/77, 78

[56] References Cited

U.S. PATENT DOCUMENTS

| | | | |
|---|---|---|---|
| 4,410,660 | 10/1983 | Straus | 435/863 |
| 4,683,195 | 7/1987 | Mullis et al. | 435/6 |
| 4,777,130 | 10/1988 | Maes | 435/863 |

FOREIGN PATENT DOCUMENTS

| | | | |
|---|---|---|---|
| 0076123 | 4/1983 | European Pat. Off. | 435/6 |
| 0168933 | 5/1985 | European Pat. Off. | 435/6 |
| 0196215 | 1/1986 | European Pat. Off. | 424/92 |
| 0079139 | 3/1986 | European Pat. Off. | 435/6 |
| 0173339 | 3/1986 | European Pat. Off. | 435/6 |
| 0229442 | 7/1987 | European Pat. Off. | 435/91 |
| 8402721 | 7/1984 | PCT Int'l Appl. | 435/6 |
| 8600019 | 1/1986 | PCT Int'l Appl. | 424/92 |
| 8800974 | 2/1988 | PCT Int'l Appl. | 530/300 |
| 8800977 | 2/1988 | PCT Int'l Appl. | 530/300 |

OTHER PUBLICATIONS

Butcher et al., Biochem. Soc. Trans. 15(3):550–551 (1987).
Eisenach et al., Am. Rev. Respir. Dis. (USA) 133(6):1065–1068 (1986) (Abst.).
McFadden et al., Biochem. Soc. Trans. 15(3):549–550 (1987).
Green et al., *Nucleic Acids Research* (1989) 17(22):9063–9073.
Moss et al., "Specific detection of *Mycobacterium paratuberculosis* by DNA hybridization with a fragment of the insertion element IS900", pre-publication submitted to Gut (1990) pp. 1–19.
Vary et al., *J. Clin. Microbiol.* (1990) 28(5):933–937.
Labidi et al., *Chem. Abstracts* (1986) 104:156.
Hamilton et al., *Mol. Gen. Gen.* (1985) 200:47–59.
Labidi et al., *Chem. Abstracts* (1986) 104:195.
Crawford et al., *Chem. Abstracts* (1986) 86:296 abstract No. 65372z.
Crawford et al., *Chem. Abstracts* (1986) 105:408 abstract No. 222283v.
Bruton et al. *Nuc. Acids Res.* (1987) 15(17):7053–7065.

(List continued on next page.)

*Primary Examiner*—Margaret Moskowitz
*Assistant Examiner*—Stephanie W. Zitomer
*Attorney, Agent, or Firm*—Reed & Robins

[57] ABSTRACT

The invention relates to a family of DNA insertion sequences (ISMY) of mycobacterial origin and other DNA probes which may be used a probes in assay methods for the identification of mycobacteria and the differentiation between closely related mycobacterial strains and species. In one method the probes are used to distinguish pathogenic *M. paratuberculosis* from *M. avium*, which finds an application in the diagnosis of Crohn's disease in humans and Johne's disease in animals. The use of ISMY, and of proteins and peptides encoded by ISMY, in vaccines, pharmaceutical preparations and diagnostic test kits is also disclosed.

26 Claims, 9 Drawing Sheets

OTHER PUBLICATIONS

Chater et al., *Mol. Gen. Gen.* (1985) 200:235–239.
Calos et al., *Cell* (1980) 20:579–595.
Kohne *Amer. Clin. Prod. Rev.* (Nov., 1986).
Cullum, J. in *Genetics of Bacteria*, 1985, (John Scaife et al., ed), Academic Press, pp. 85–95.
Goodfellow et al., (1982) in *The Biology of Mycobacteria* (ed. Ratledge and Stanford), Academic Press, London, pp. 471–521.
Graham et al., (1987) Gastroenterology 92:436–442.
Chiodini et al., in the Cornell Veterinarian 74:218–262.
Collins, (1986) Int. J. Leprosy 54(3):458–474.
van Eden et al., (1988) Nature 331:171–173.
Chiodini et al., (1984) Digestive Diseases and Sciences 29(12):1073–1079.
McFadden et al., (1987) Journal of Clinical Microbiology 25(5):796–801.
McFadden et al., (1987) Molecular Microbiology 1(3):283–291.
Collins et al., (1987) Gastroenterology 92(5):1352.
Martin et al., (1987) Am. Rev. Respir. Dis. 136:344–348.
McClure et al., (1987) J. Infectious Diseases 155(5):1011–1019.
Scharf et al., (1987) Science 233:1076–1078.

Fig. 4.

CONTIG 1

●CAGCTGGGTG ACGGCTTCCC ACACGTCGGG CACCTCGTCC AGCGGAACCC
ACACGCTGAG CCGCTGGGCC AGCATCGGGT TGGTGGACAG GCCGCCGCCC
ACCCACAGGT CCAGGCCGGG TCCGTGCTCG GGGTGCTCGA CGCCGACGAA
CGCGACGTCG TGGGTCTCGT GCGAGACGTC CTGCAGGCCC GAGACCGCGG
TTTTGTACTT GCGCGGCAGG TTGGCGTATT CGGGGTTGTT CAGGGAGCGA
CGGACGATCT CCTCGATCGC GGGCGACGGA TCGAGCACCT CGTCGAGCGA
GTGCCGGCCA GCGGCAGCC GTGGATGCCG CGCGGGCAGT CCGCGCAGGC
CTCGGTGGTC TGCAGCCCGA CGGACTCGAG CCGTCGCCAG ATCTCGGGCA
CGTCCTCGAT GCGAATCCAG TGCAGCTGCA GGTTTTCCCG GTCGCTGATA
TCGGCGGTGT CGCGGGCGAA TTCGGTGGAG ATCTGGCCGA GCGTGCGCAT
GGTGTGCGCC GACATCGCCT TGCCGTCGGA GCGGACCCGC ATCATGAAGT
ACTTGGCTTC GATCTTGTCG GTGTTGTCGT CACCGGTCCA GCTGCCGTCG
TAGCCCTGCT CGCGTTGGGT GTACAGGCCC ATCCACCGGA AGCGGCCGCG
CAGGTCGGAC TTGTCGATGC TGTCGAAACC CTGCTTGGCG TAGACGTTGA
TGATGCGCTC GCATCGCCGA TCTCGTTCAG CGGCCCGTCG GCCAGCTTGA
TCTTCTCGGT GTCGTTGAGC GGTTCGCGAT CTCCCAGCGA GCCCAGACCT
GACCCTCAGT TGCGGGTCTT GACGGGACGT GCGGTGGTCA TGTGGTGTTC
CTTACCTTTC TTGAAGGGTG TTCGGGGCCG TCGCGCTTAG GCTTCGAATT
GCCCAGGGAC GTCGGGTATG GCTTTCATGT GGTTGCTGTG TTGGATGGCC
GAAGGAGATT GGCCGCCCGC GGCGTCCCGC GACGACTCGA CCGCTAATTG
AGAGATGCGA TTGGATCGCT GTGTAAGGAC ACGTCGGCGT GGTCGTCTGC
TGGGTTGATC TGGACAATGA CGGTTACGGA GGTGGTTGTG GCACAACCTG
TCTGGGCGGG CGTGGACNCC GGTAAGCGCG ACCATTACTG CATGGTTATT
AACGACGACC GACNCGCGCA CGATTGCTCT CGCAGCGGGT GGCCAACGAC
GAGGCCGCGC TGCTGGAGTT TGATTGCGGC GGTGACGACG TTGGCCGATG
GAGGCGAGGT▶

Fig.4 (continued)

CONTIG 2

●GATCGACCTC ACAGCCGGCG GAGCCGGTTC GTGACTCGCT TCGTCCATGT
CCGGGCAGCG GCTGCTTTAT ATTCCCGGGC GCACGGTCCA TCCAGCGGGT
AGTTACCGCG GCGAAGGCAA GACCGACGCC AAAGACGCTG CGATCATCGC
CGATCAGGCC CGGATGCGCC ACGACTTGCA GCCTCGTGCG CGCCGGCGAT
GACATCGCAG TCGACGTGCG CATCCTGACC AGCCGACGTT CCGATCTGGT
GGCTGATCGG ACCCGGGCGA TCAACCGAAT GCGCGCCCAG CTGCTGGAAT
ACTTTCGGCG CTGGAACGCG CCTTCGACTA CAACAAGAGC CGTGCCGCGC
TGATCCTGCT TACTGGCTAC CAAACTCCCG ACGCGCTGCG TAGCGCCGGT
GGCGCTCGAG TAGCCGCGTT CTTGCGTAAA CGAAGAGGGC CCGCAACGCC
GATCACCGTC GCAGCCACCG CGCTGCAGGC CGCTAACGCC CAACACAGCA
TCGTGCCCGG CCAACAACTG GCGGCCACTG TGGTGGCCCG CCTGGCCAAG
GAGGTGATGG CCCTCGACAC CGAAATCGGC GACCACGACC GACGCGATGA
TCGAGGAGCG ATTTCGCCGC CACCGCCACG CCGAAATTCA TCCTGAGCAT
TGCCCGGATT CGGCGTCATC CTGGGCGCTG AGTTCCTCGC CACCGGCGGG
GACATGGCCG CATTCGCCTC CGCCGACCGC CTCGGCGTCG CGGCCTGGCC
TGGCGCCGGT ACCACGAGAT TCCGGCGCAT CAGCGGAAAC CTCAAACGCC
CCCGACGCTA CGACCGGCGC CTGCTGCCGG CCTGCTACCT GTCGGCCTTG
GTCAGCATCC GCACCGACCC CTCCTCGCGC ACCTACTACG ACCGAAAACG
CACCGAAGGA AAACGCCACA CCCAAGCCGT CCTCGCCCTG GCCCGCCGCC
GCCTCAACGT CCTGTGGGGC CATCGTGCGC GACCACGCTG TCTACCACCC
CGCAACCACT ACCGCGGCGG CTTGACAACG TCATTGAGAA TCTCCTTCGC
GAACATTCCC CGGTGTGCGA CGCACCGGGG TGGTGTTCCT GACGGCGGCT
CAGATCGGCC TGCTACGGGG CCGGGATGGG CTGTCGGCCG CGGCATCGCG
ATGATGTTGG GGCTTTAGGC ACCCGCAAGT TCGTCGTTGG ACCCACGGGT
CGCGATTCCC ATAGTGCACT ACTTGCGGCC GCGTCAGTAG AGGTCGCATG
TTGTGAGGGC ACAACCGGAC GTTGTGTGCC GCCGCTTCAC GATGGGTGAC
GGCGATCACT TTGCGGGCCA GGCGAATTGC CGGGCCGGTC GCTGCCGTGA
GGTTGGCAAT TCCGGCCTGA TTGGCAACCT TGGTCAGGCC GGGCGTCAGA
CCGAATCCCG TGGCGGAACG TCCGTTCTGC GGCCGCCGAG TTGGGCCGGC
AGCGGGTGTA TCCGTGCAAT GTTGATCAGC GACCGCCGTT GCGGGCGGCG
GT▶

```
TCCTTACCTTTCTTGAAGGGTGTTCGGGGCCGTCGCTTAGGCTTCGAATTGCCCAGGGAC
         10        20        30        40        50        60

GTCGGGTATGGCTTTCATGTGGTTGCTGTGTTGGATGGCCGAAGGAGATTGGCCGCCCGC
         70        80        90       100       110       120

GGTCCCGCGACGACTCGACCGCTAATTGAGAGATGCGATTGGATCGCTGTGTAAGGACAC
        130       140       150       160       170       180
                                                 SD         V
GTCGGCGTGGTCGTCTGCTGGGTTGATCTGGACAATGACGGTTACGGAGGTGGTTGTGGC
        190       200       210       220       230       240

A  Q  P  V  W  A  G  V  D  A  G  K  A  D  H  Y  C  M  V  I
ACAACCTGTCTGGGCGGGCGTGGACGCCGGTAAGGCCGACCATTACTGCATGGTTATTAA
        250       260       270       280       290       300

N  D  D  A  Q  R  L  L  S  Q  R  V  A  N  D  E  A  A  L  L
CGACGACGCGCAGCGATTGCTCTCGCAGCGGGTGGCCAACGACGAGGCCGCGCTGCTGGA
        310       320       330       340       350       360

E  L  I  A  A  V  T  T  L  A  D  G  G  E  V  T  W  A  I  D
GTTGATTGCGGCGGTGACGACGTTGGCCGATGGAGGCGAGGTCACGTGGGCGATCGACCT
        370       380       390       400       410       420

L  N  A  G  G  A  A  L  L  I  A  L  L  I  A  A  G  Q  R  L
CAACGCCGGCGGCGCCGCGTTGCTGATCGCCTTGCTCATCGCTGCCGGGCAGCGGCTGCT
        430       440       450       460       470       480

L  Y  I  P  G  R  T  V  H  H  A  A  G  S  Y  R  G  E  G  K
TTATATTCCCGGGCGCACGGTCCATCACGCCGCGGGTAGTTACCGCGGCGAAGGCAAGAC
        490       500       510       520       530       540

T  D  A  K  D  A  A  I  I  A  D  Q  A  R  M  R  H  D  L  Q
CGACGCCAAAGACGCTGCGATCATCGCCGATCAGGCCCGGATGCGCCACGACTTGCAGCC
        550       560       570       580       590       600

P  L  R  A  G  D  D  I  A  V  E  L  R  I  L  T  S  R  R  S
TCTGCGCGCCGGCGATGACATCGCAGTCGAGCTGCGCATCCTGACCAGCCGACGTTCCGA
        610       620       630       640       650       660

D  L  V  A  D  R  T  R  A  I  E  P  N  A  R  P  A  A  G  I
TCTGGTGGCTGATCGGACCCGGGCGATCGAACCGAATGCGCGCCCAGCTGCTGGAATACT
        670       680       690       700       710       720

L  S  A  L  E  R  A  F  D  Y  N  K  S  R  A  A  L  I  L  L
TTCGGCGCTGGAACGCGCCTTCGACTACAACAAGAGCCGTGCCGCGCTGATCCTGCTTAC
        730       740       750       760       770       780
```

FIG. 6-1

```
T   G   Y   Q   T   P   D   A   L   R   S   A   G   G   A   R   V   A   A   F
TGGCTACCAAACTCCCGACGCGCTGCGCAGCGCCGGTGGCGCTCGAGTAGCCGCGTTCTT
      790       800       810       820       830       840

L   R   K   R   K   A   R   N   A   D   T   V   A   A   T   A   L   Q   A   A
GCGTAAACGCAAGGCCCGCAACGCCGATACCGTCGCAGCCACCGCGCTGCAGGCCGCTAA
      850       860       870       880       890       900

N   A   Q   H   S   I   V   P   G   Q   Q   L   A   A   T   V   V   A   R   L
CGCCCAACACAGCATCGTGCCCGGCCAACAACTGGCGGCCACTGTGGTGGCCCGCCTGGC
      910       920       930       940       950       960

A   K   E   V   M   A   L   D   T   E   I   G   D   T   D   A   M   I   E   E
CAAGGAGGTGATGGCCCTCGACACCGAAATCGGCGACACCGACGCGATGATCGAGGAGCG
      970       980       990      1000      1010      1020

R   F   R   R   H   R   H   A   E   I   I   L   S   M   P   G   F   G   V   I
ATTTCGCCGCCACCGCCACGCCGAAATCATCCTGAGCATGCCCGGATTCGGCGTCATCCT
     1030      1040      1050      1060      1070      1080

L   G   A   E   F   L   A   A   T   G   G   D   M   A   A   F   A   S   A   D
GGGCGCTGAGTTCCTCGCCGCCACCGGCGGGGACATGGCCGCATTCGCCTCCGCCGACCG
     1090      1100      1110      1120      1130      1140

R   L   A   G   V   A   G   L   A   P   V   P   R   D   S   G   R   I   S   G
CCTCGCCGGCGTCGCCGGCCTGGCGCCGGTACCACGAGATTCCGGCCGCATCAGCGGAAA
     1150      1160      1170      1180      1190      1200

N   L   K   R   P   R   R   Y   D   R   R   L   L   R   A   C   Y   L   S   A
CCTCAAACGCCCCCGACGCTACGACCGGCGCCTGCTGCGCGCCTGCTACCTGTCGGCCTT
     1210      1220      1230      1240      1250      1260

L   V   S   I   R   T   D   P   S   S   R   T   Y   Y   D   R   K   R   T   E
GGTCAGCATCCGCACCGACCCCTCCTCGCGCACCTACTACGACCGAAAACGCACCGAAGG
     1270      1280      1290      1300      1310      1320

G   K   R   H   T   Q   A   V   L   A   L   A   R   R   R   L   N   V   L   W
AAAACGCCACACCCAAGCCGTCCTCGCCCTGGCCCGCCGCCGCCTCAACGTCCTGTGGGC
     1330      1340      1350      1360      1370      1380

A   M   L   R   D   H   A   V   Y   H   P   A   T   T   T   A   A   A
CATGCTGCGCGACCACGCTGTCTACCACCCCGCAACCACTACCGCGGCGGCTTGACAACG
     1390      1400      1410      1420      1430      1440

TCATTGAGAAT
     1450
```

FIG. 6-2

DIAGNOSTICS FOR MYCOBACTERIA IN PUBLIC HEALTH, MEDICAL, AND VETERINARY PRACTICE

This application is a continuation, of application Ser. No. 185,113, filed Apr. 22, 1988 now abandoned.

INTRODUCTION

It is estimated that 3 to 6 million people in the world die each year from leprosy and tuberculosis alone. Human disease due to atypical mycobacteria is increasing. Tuberculosis and paratuberculosis are common in livestock, account for major economic losses, and form a reservoir of infection for human disease. Despite BCG vaccination and some effective drugs, mycobacterial disease remains a major global problem.

Present methods for the identification and characterisation of mycobacteria in samples from human and animal diseases are by Zeil-Neilson staining, in-vitro and in vivo culture, biochemical testing and serological typing [1]. These methods are generally slow and do not readily discriminate between closely related mycobacterial strains and species particularly, for example, *Mycobacterium paratuberculosis* and *Mycobacterium avium*. Mycobacteria are widespread in the environment, and rapid methods do not exist for the identification of specific pathogenic strains from amongst the many environmental strains which are generally non-pathogenic. Difficulties with existing methods of mycobacterial identification and characterisation have increased relevance for the analysis of microbial isolates from Crohn's disease (Regional Ileitis) in humans [2] and Johne's disease in animals [3] (particularly cattle, sheep and goats) as well as for *M. avium* strains from AIDS patients with mycobacterial superinfections [4]. Although recognition of the causative agents of human leprosy and tuberculosis are clear, clinico-pathological forms of each disease exist, such as the tuberculoid form of leprosy, in which mycobacterial tissue abundance is low and identification correspondingly difficult. Improvements in the specific recognition and characterisation of mycobacteria may also increase in relevance if current evidence linking diseases such as rheumatoid arthritis to mycobacterial antigens is substantiated [5]. Emerging drug resistance to mycobacteria including *M. avium* isolates from AIDS patients, any *Mycobacterium tuberculosis* from TB patients is an increasing problem. Rapid methods for the identification of mycobacteria in environmental and disease samples, for the specific recognition of pathogenic strains, for precisely distinguishing closely related mycobacterial strains, and for defining resistance patterns to antimycobacterial agents are badly needed.

SUMMARY OF THE INVENTION

A method of using DNA probes for the precise identification of mycobacteria and discrimination between closely related mycobacterial strains and species by genotype characterisation. The method of genotypic analysis is further applicable to the rapid identification of phenotypic properties such as drug resistance and pathogenicity.

DNA probes of the invention are derived from recombinant DNA libraries or synthesised using DNA sequence information from recombinant DNA clones derived from different mycobacterial strains and species. DNA clones are selected for their ability specifically to identify mycobacterial DNA from other microbial DNA. DNA probes of the invention are also selected for their ability to distinguish and differentiate between closely related mycobacterial strains and species such as *Mycobacterium paratuberculosis* and *Mycobacterium avium*, and different strains of mycobacteria including those isolated from AIDS patients. DNA probes of the method of the invention are also selected for their ability to identify and predict mycobacterial phenotypes, including drug resistance, by genotype characterisation.

DETAILED DESCRIPTION OF THE INVENTION

1. DNA probes for the specific identification of Mycobacteria.

We have identified, for the first time, a family of related DNA insertion sequences (ISMY) in the genome of disease isolates of mycobacteria. The first example of ISMY (ISMY-1) we identified and characterised in the clone pMB22 (Deposited with the National Collections of Industrial and Marine Bacteria NCIB number 12461 at Torry Research Station, P.O. Box No. 31, 135 Albany Road, Aberdeen, AB9, 8DG, Scotland,) from a genomic DNA library derived from a mycobacterial isolate from Crohn's disease (CD). This clone contains the full ISMY-1 sequence. We also identify ISMY-1 in *Mycobacterium paratuberculosis* cultured from cattle and other animals suffering from Johne's disease (JD). We identify related sequences of the ISMY family in mycobacterial disease isolates superinfecting humans with AIDS (acquired immune deficiency syndrome), atypical mycobacterial pneumonias in immunocompetent humans, and other mycobacterial disease isolates from animals and birds. We also identify ISMY in isolates of *Mycobacterium leprae* and *Mycobacterium lepraemurium*. ISMY sequences appear to be prevalent in pathogenic mycobacteria, but have not been identified in saprophytic mycobacteria.

2. Diagnostics and vaccines for public health, medical and veterinary use based upon Mycobacterial Insertion Sequences (ISMY).

All or part of the DNA sequence of each member of the ISMY family may be used with or without enzymic amplification by polymerase chain reaction (PCR) or other techniques, as DNA or RNA probes in diagnostics for the specific recognition of pathogenic mycobacteria in environmental and disease samples and in in-vitro mycobacterial cultures. All or part of the proteins or peptides encoded, mutated or modified in expression by ISMY may be used in immunodiagnostics or other diagnostics for a similar purpose whether based on recombinant proteins or synthetic peptides. Such ISMY derived proteins or peptides may also be used as specific vaccines for the prevention of mycobacterial disease in medical and veterinary practise. Alteration of microbial phenotype by deletion or transfection of ISMY in whole or in part may be used to engineer cultivateable microbial strains suitable for use as vaccines, in immunotherapy or diagnostics.

SUMMARY OF THE FIGURES

FIG. 1 also shows a different and much simpler banding pattern with restricted genomic DNA from 4 other species of mycobacteria which do not contain ISMY-1 or homologous insertion sequences conferring pathogenicity. This figure illustrates how a shared and complex banding pattern can demonstrate identity between mycobacteria as between CD and JD isolates, as well as distinguish precisely between different mycobacteria.

DNA was extracted from Crohn's disease-derived strains: Ben (CD1), Linda (CD2) & Dominic (CD3); *M. paratuberculosis, M. avium* complex serotype 2, *M. avium* complex serotype 5, *M. kansasii*, and *M. phlei*. DNA samples (1 g) were digested with restriction endonuclease pvuII, electrophoresed through 1% agarose, blotted onto a nylon membrane, hybridized to radiolabeled probe pMB22 and autoradiographed. Molecular weight markers, in kilobases are shown on the right.

Figure 1:
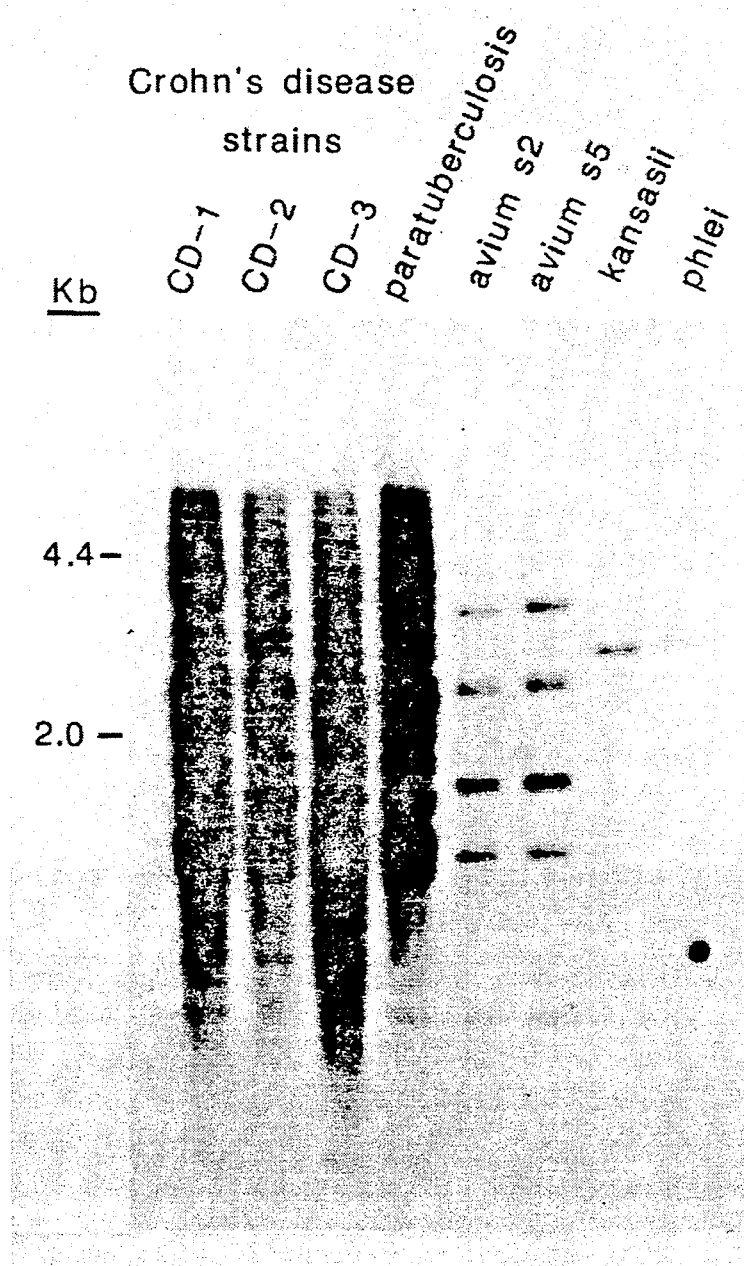
FIG. 1 shows the multiple banding pattern or DNA "fingerprint" obtained when restricted genomic DNA from each of three separate Crohn's disease (CD) mycobacterial isolates and one Johne's disease (JD) *M. paratuberculosis* isolate are probed with pMB22 containing ISMY-1 of the invention.
Figure 2:
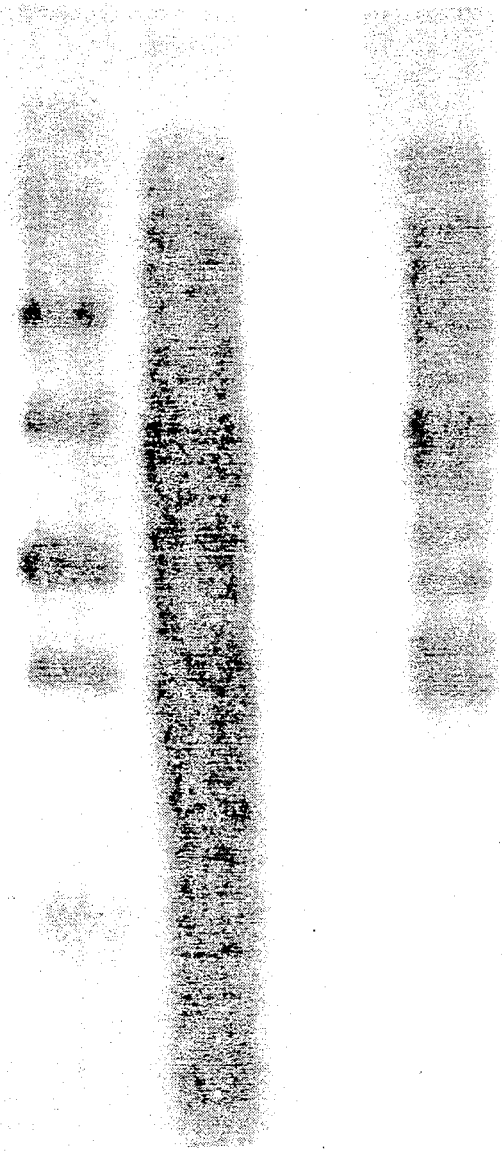
Figure 3A:
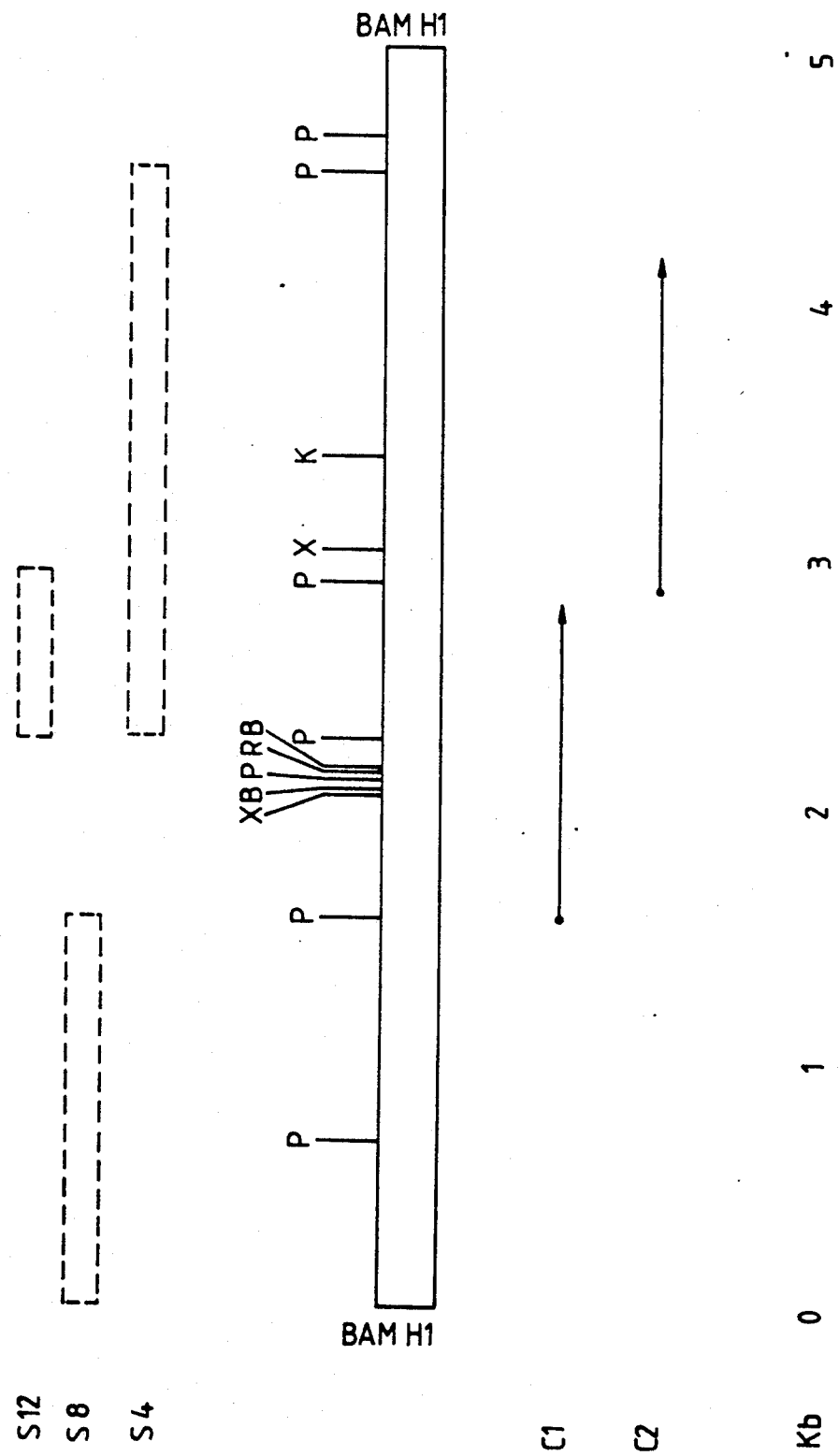

FIG. 2 supports FIG. 1 by showing identity between further independent CD mycobacterial isolates from Amsterdam, Holland and Los Angeles, U.S.A. both being different from *M. avium*. DNA was extracted from Crohn's disease-derived strains 410 (obtained from G. Gitnick) and strain H1 (obtained from J. Haagsma); and *M. avium*. DNA samples (1 g) were digested with restriction endonuclease PvuII, electrophoresed through 1% agarose, blotted onto a nylon membrane, hybridized to radiolabeled probe pMB22 and autoradiographed. Lane 1: *M. avium*, lane 2: strain H1, lane 3: strain 410. FIG. 3A shows a restriction map which characterises the 5 kb of insert DNA containing the sequence ISMY-1 of the invention, in the clone pMB22. Restriction endonuclease map of pMB22 showing location of sequencing contigs C1 and C2 (→), and also location of subclones S4, S8 and S12 (=====). The exact location of subclones has not been determined, therefore their maximum extent is indicated by blocked lines. P=PvuII, X=XhoI, R=EcoRI, B=BglII, K=KpnI. Molecular weight is indicated in kilobases (Kb).

FIG. 3 also shows mapping data of the loci encoding sequences contained in pMB22 in the genomes obtained from *M. avium* and *M. paratuberculosis* DNA indicating that DNA flanking ISMY-1 in *M. paratuberculosis* is identical to DNA found at the same site in *M. avium* but without of course, an associated ISMY-1. This indicates that ISMY-1 is inserted into the genome of *M. paratuberculosis* at this site and is a likely cause of the divergent phenotype. Molecular weight is shown in kilobases (Kb).

FIG. 4 further characterises the insert cloned in pMB22 with partial DNA sequence data spanning the ISMY-1 insertion element. The sequence of ISMY-1 is contained within the two sequences starting at CONTIG 1 837 nucleotide and ending at CONTIG 2 of 1038 nucleotide. The locations are also shown in FIG. 3A.

Figure 5:
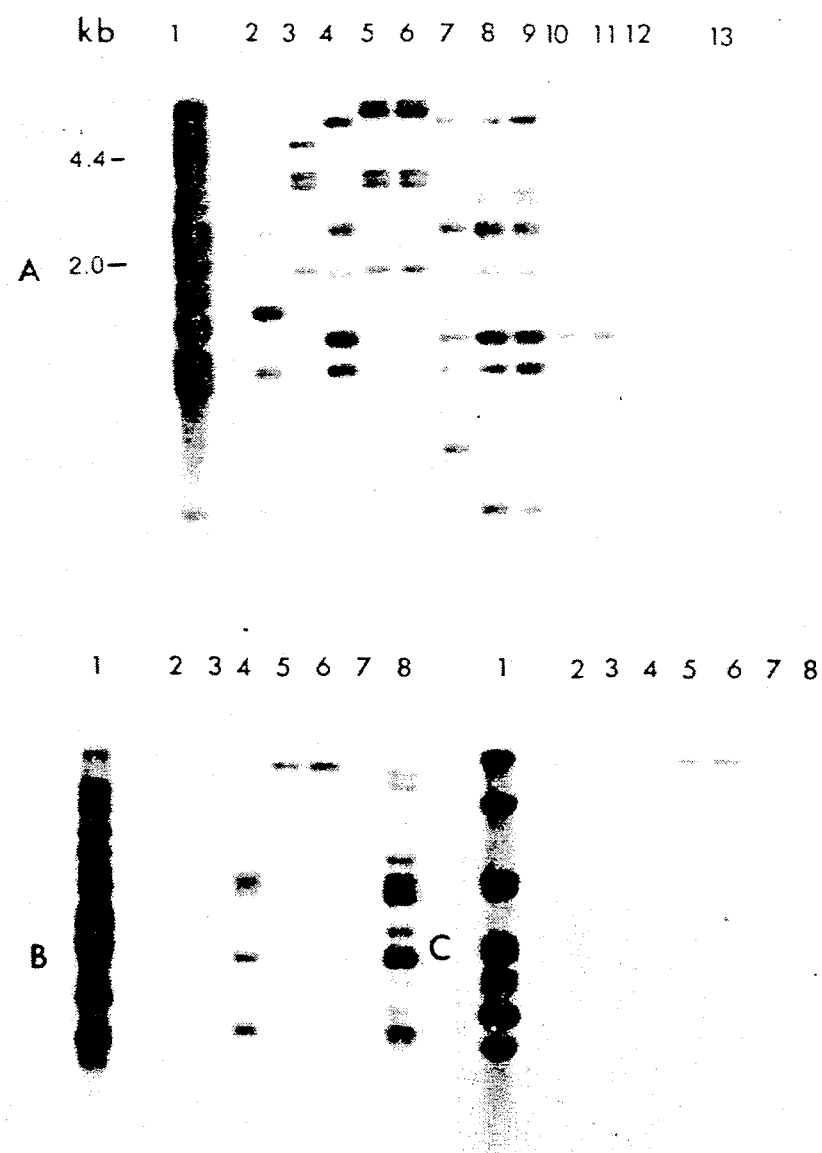

FIG. 5 shows the multiple banding patterns obtained from a series of pathogenic strains of *M. avium* which are shown to contain other ISMY sequences related to the insertion sequence ISMY-1 found in pMB22. These related ISM sequences may be involved in pathogenicity of these and other mycobacteria, particularly those of the *M. avium* complex. FIG. 5 also demonstrates the use of DNA fingerprinting to identify further pathogenic mycobacteria and distinguish them from environmental mycobacteria. DNA was extracted from mycobactin-dependent disease-derived strains of *M. avium, M. paratuberculosis* and atypical *M. avium* strains. DNA samples (approx. 0.5 g) were digested with restriction endonuclease PvuII, electrophoresed thorough 1% agarose, blotted onto nylon membrane and hybridized to radiolabeled, pMB22 probe (A), pMB22/S4 probe (B) pMB22/S12 probe (C), and autoradiographed. DNA samples were: *M. paratuberculosis* (lane 1), non-mycobactin- dependent *M. avium* serotype 2 (lane 2), non-mycobactin-dependent armadillo-derived strain 10911 (lane 3), mycobactin-dependent goat-derived strain 8589 (lane 4), mycobactin-dependent armadillo-derived strains 157 (lane 5) and 157S (lane 6), mycobactin-dependent porcine-derived strain 7941 (lane 7), mycobactin-dependent deer-derived strains 8446 (lane 8) and 8438 (lane 9), mycobactin-dependent wood-pigeon-derived strains 1/79 (lane 10), 5/79 (lane 11), 1/72 (lane 12) and mycobactin-dependent goat-derived strain GK27 (lane 13). Molecular weight markers are shown on the right of A.

FIG. 6 illustrates the nucleotide sequence of insertional sequence ISMY-1 and the amino acid sequence of open reading frame, ORF 1197, and includes nine nucleotides connecting the contig 1 and contig 2 of FIG. 4. These are shown at nucleotides 403–411.

THE FOLLOWING EXAMPLES ILLUSTRATE THE INVENTION

EXAMPLE 1

DNA probes for the specific identification of mycobacteria

DNA probes were derived as follows. Genomic DNA from a strain of *M. paratuberculosis* isolated from a human CD patient [6] was digested with Bam H1, ligated into the plasmid vector pGEM-1 (Promega-Biotech), and used to transform *E. coli* DH1 cells using standard techniques (Maniatis et al. 1982. Molecular Cloning: Laboratory Manual). Greater than 20,000 ampicillin resistant recombinant clones were obtained. Insert size in plasmid DNA from 12 randomly selected clones (pMB1 to 12) ranged from 180 bp to 4200 bp. This library was screened by hybridisation with hexanucleotide primed, radiolabelled total genomic DNA probes from *M. paratuberculosis* strain Ben, *M. paratuberculosis* (ATCC 19698), and *M. kansasii* (TMC 1201) Hybridising colonies were identified by autoradiography. Approximately 5% of clones hybridised to both *M. paratuberculosis* (ATCC 19698) and *M. paratuberculosis* (strain Ben) and 1% to *M. kansasii*. Forty eight clones were selected as giving either a differential hybridisation signal with DNA from the three sources, or a similar signal with DNA from the three sources, and gridded onto an ordered array. The ordered array was again hybridised with radiolabelled genomic DNA from *M. paratuberculosis* strain Ben, *M. paratuberculosis* (ATCC 19698), *M. avium* complex serotype 2 (Caddigg 16741), *M. avium* complex serotype 5 (25546-759) *M. kansasii* (TMC 1201) and *M. phlei* (NCIB 8573). Clones designated pMB13 to 24 were selected as showing either strong hybridisation to all DNA samples, or demonstrating differential hybridisation between the DNA samples.

EXAMPLE 2

DNA probes for 16s ribosomal RNA

Probes encoding ribosomal RNA sequences were isolated by screening the *M. paratuberculosis* strain Ben genomic library with radiolabelled complementary DNA (cDNA) prepared from total RNA extracted from *M. avium* serotype 2 cells. Cells were lysed by sonication for 80 second in 4M guanidinium isothiocyanate and RNA purified by centrifugation through 5.7M caesium chloride and precipitated with 70% ethanol. Radiolabelled cDNA was prepared by incubating 1 μg of purified RNA with reverse transcriptase, using random hexanucleotides to prime cDNA synthesis. The radiolabelled probe was hybridised to the bacterial colonies in situ. Autoradiography revealed hybridising clones which were picked and plasmid DNA extracted. This was radiolabelled and used to probe Northern blots of M. avium tool RNA. A clone designated pMBr16 was found to hybridise strongly to 16S ribosomal RNA on Northern analysis.

EXAMPLE 3

DNA probes for M. bovis and M. leprae

In a further example of the preparation and use of DNA probes for the recognition and differentiation of a specific mycobacterial strain, DNA from Mycobacterium bovis (BCG) strain Glaxo was digested with Bam H1, ligated to vector pGEM-1 and used to transform E. Coli DH1 cells by standard techniques as before. The resulting genomic DNA library was probed with radiolabelled M. bovis genomic DNA and strongly hybridising clones designated pMBCG13-24 picked. Similarly, genomic DNA was extracted from two nude mouse isolates of Mycobacterium leprae obtained from lepromatous leprosy patient tissue and a genomic library of several thousand clones prepared. Twelve randomly selected clones containing inserts and designated pML1-12 were isolated.

EXAMPLE 4

The use of mycobacterial DNA probes

The precise identification and differentiation between mycobacterial strains and species is in general performed by the isolation of genomic DNA from target bacteria, digestion with restriction endonucleases, electrophoresis, and Southern blotting using one of the mycobacterial DNA probes radiolabelled as described. Autoradiography reveals banding patterns that are examined for restriction fragment length polymorphisms (RFLPs) but dot blot analyses and non radioactive revealing systems as well as PCR amplification may also be employed. RFLPs are also used to measure DNA base substitution between strains and species.

Differentiation between M. paratuberculosis and M. avium complex. DNA from M. paratuberculosis ATCC 19698, M. paratuberculosis strain Ben, and M. avium serotype 2 (Caddig 16741), was digested with restriction endonucleases Bam H1, EcoR1, Bst 1, Ava 1, Pst 1, Hinf 1, Hae III, Sau 3A, Hinc 1, Pvu 11, Pvu 1 and Taq 1, electrophoresed, blotted and probed with radiolabelled clones, pMB7, pMB12, pMB16, pMB17, pMB19, pMB20, pMB21, pMB22, and examined for RFLPs that distinguished between the DNA samples. (The derivation of clone pMB22 which contains the insertion sequence ISMY-1 of the invention, is described in example 5). Several RFLPs were found to distinguish between the M. avium and the M. paratuberculosis strains [7]. However, no RFLPs were found to distinguish between M. paratuberculosis ATCC 19698 and M. paratuberculosis strain Ben including the complex banding pattern seen with pMB22 containing the ISMY-1 insertion sequence [7], suggesting genetic identity between these two.

The vaccine strain 18 presumed to be of M. paratuberculosis was further shown in fact to be identical to M. avium serotype 1 [8].

Identification of Crohn's disease (CD) derived mycobacteria. Several isolates of mycobacteria from CD tissue have been through to be related to M. paratuberculosis [6, 9]. However, conventional techniques, which are incapable of distinguishing precisely between M. paratuberculosis and M. avium (particularly mycobactin-dependent M. avium) have left the identity of these CD isolates uncertain. Since M. avium complex strains can be isolated from healthy subjects, and are common environmental organisms [10], the exact identity of the CD-derived strains is critical to an evaluation of their etiological significance in CD. DNA was therefore extracted from three CD-derived status (Ben, Linda and Dominic) [6], and also M. avium complex serotype 2, M. avium complex serotype 5, M. kansasii and M. phlei. DNA was digested with restriction endonucleases and probed with DNA clones of the invention identifying RFLPs as described that differentiated between M. paratuberculosis and M. avium complex serotype 2. Six different RFLPs were investigated. Each of the three CD-derived strains were shown to be identical to M. paratuberculosis [7] (FIG. 1). These findings were supported by the use of the ISMY-1 containing clone pMB22 of the invention to probe restricted DNA from two further uncharacterised human CD mycobacterial isolates, 410 & H1 obtained from two independent laboratories, of Drs Gitnik and Beaman, UCLA in the U.S.A. and Dr. J. Haagsma, National Veterinary Institute, Amsterdam, Netherlands, respectively. Identical banding patterns were obtained showing that these further CD isolates were again ISMY-1 containing M. paratuberculosis. (FIG. 2).

Similar methods and DNA probes of the invention were used to examine the identity of 8 strains of M. paratuberculosis isolated from infected cows with Johne's disease. Isolates were derived independently from infected animals in the UK, France and the U.S.A., as well as 2 additional isolates from Macaque monkeys suffering from a disease resembling Johne's disease [11]. RFLP analysis with probes pMB14, pMB20, and pMB22 revealed that all strains gave identical banding patterns to those seen in FIGS. 1 and 2 for pMB22, demonstrating the conserved nature of the pathogen M. paratuberculosis. Probing with clone pMB22 containing insertion sequence ISMY-1, revealed identical banding patterns for each strain.

Members of the M. avium complex of mycobacteria have been difficult to characterise and define by conventional techniques. We used the mycobacterial probes and methods of the invention described, to examine a range of M. avium complex strains. Several different patterns were obtained [8]. Serotypes 2, 4, 5, 6 and 8 were found to be similar with less than 2% DNA based substitution between strain types. However, at least 6 strain type banding patterns were recognised. M. avium complex serotypes 11, 16 and 27 were found to have greater than 13% DNA base substitution between each other and the serotype 2,4,5,6,8 group. These strains were previously designated M. intracellulare or intermediate strains. We proposed from this work that M. avium complex strains giving banding patterns similar to those obtained with serotypes 2,4,5,6 and 8 to be designated M. avium and the heterogenous strains represented by serotypes 11, 16 and 27 be designated M. intracellulare complex [8]. Strain typing using the higher resolution DNA probe methods of the invention did not always correspond with conventional serotyping.

The methods and DNA probes of the invention were further used to distinguish *M. bovis* BCG (Glaxo) and *M. tuberculosis* strain H37RV. DNA from these mycobacteria was digested with Ava 1, Sma 1, Kpn 1, Pvu II and Pst 1, electrophoresed, blotted and probed with pMBr16 and pMBCG13. pMBr16 demonstrated a RFLP between Kpn 1 digested of *M. bovis* and *M. tuberculosis* DNA and pMBCG13 revealed an RFLP with Sma 1 digested DNA.

Similar techniques were applied to the characterisation of *M. leprae*. *M. leprae* DNA was cut with Pvu II electrophoresed, blotted and probed with pMBr16 and pML1. pML1 gave a banding pattern with *M. leprae* DNA but did not hybridise to DNA from other mycobacteria. pMBr16 gave an *M. leprae* banding pattern distinct from those seen with any other mycobacteia tested.

DNA was extracted from a range of mycobacteria, digested with Pvu II, electrophoresed, blotted, and probed with radiolabelled clone pMBr16 and other clones. The results demonstrated that each mycobacterial species gave a distinct and identifiable DNA banding pattern.

The use of cloned DNA probes of the invention for the specific identification of mycobacteria is also applicable to DNA extracts of tissues infected in vivo with mycobacteria. To demonstrate this, we extracted mouse liver infected with *Mycobacterium lepraemurium* using methods we developed to extract mycobacterial DNA [8]. Extracted DNA was cut with Pvu II electrophoresed, blotted and probed with pMB12, pMB16, pMB20 and pMB22. Specific banding patterns were obtained for *M. lepraemurium* from mouse liver which showed this organism to be closely related to *M. avium* having an approximate 2% base substitution between it and *M. avium* complex serotype 2 [8].

EXAMPLE 5

The identification, cloning and characterisation of mycobacterial insertion sequences (ISMY) of the invention Insertion sequences and transposons are short repetetive pieces of DNA within genomic DNA, which may be mobile in response to apropriate environmental conditions. They exert their biological effects either through the components which they encode or by their influence on neighbouring host genes or host genes into which they become inserted. These elements occur widely in nature and have been identified in some bacteria, yeasts, plants, insects and animals [12]. They have not hitherto been identified in mycobacteria.

A major aspect of the present invention comprises the identification, for the first time, of a novel family of related insertion sequences in disease isolates of mycobacteria. This family of insertion sequences is designated ISMY, and an example of ISMY, (ISMY-1) we have cloned and characterised in detail. Members of the ISMY family of mycobacterial insertion sequences of the invention are identified by sharing partial sequence homology and hybridising at low stringency with ISMY-1 in the clone pMB22 deposited with the National Collections of Industrial and Marine Bacteria, number 12461 at Torry Research Station, P.O. Box No. 31, 135 Abbey Road, Aberdeen, AB9, 8DG, Scotland, U.K. All or part of the DNA or RNA encoded by members of the ISMY family and all or part of the proteins and peptides encoded by ISMY or mutagenised or altered in expression by ISMY are applicable to use in a novel range of diagnostics for disease-causing mycobacteria containing ISMY. ISMY of the invention are also used by specific deletion or transfection, to generate mutant or recombinant bacteria or viruses for the provision of novel vaccines, agents for immunotherapy, or diagnostics.

Genomic DNA from a Crohn's disease isolate of *Mycobacterium paratuberculosis* was used to generate a genomic DNA recombinant library using the plasmid vector pGEM-1 and *E. coli* DH1 cells by standard techniques as described. This library was screened with radiolabelled DNA probes derived from *M. paratuberculosis, M. kansasii* and *M. avium*. There was only one clone identified which hybridised strongly to *M. paratuberculosis* but only weakly to *M. avium* and *M. kansasii* DNA and we designated this clone pMB22. This was picked and found to contain an insert of about 5 kb. This recombinant DNA fragment was excised, purified, digested with further restriction endonucleases, and subcloned into either the plasmid vector, pGEM-1, or the M13 phage vectors mp18 and mp19. Resulting clones were hybridised to *M. paratuberculosis* DNA and strongly positive clones were identified. The location of selected subclones, within the 5 kb insert in pMB22, some of which hybridised strongly with *M. paratuberculosis* DNA, are shown (FIG. 3A). *E. coli* strain DH1 harbouring pMB22 was deposited on Apr. 24, 1987 under Budapest treaty conditions, with the National Collections of Industrial and Marine Bacteria, Aberdeen, Scotland, U.K. where it was given the deposit number NCIB 12461.

EXAMPLE 6

Insertion sequence ISMY-1 in *M. paratuberculosis*

This section cites evidence showing that IBMY-1 in *M. paratuberculosis* are insertion sequences and that these segregate with the pathogenicity of this organism.

*M. paratuberculosis* DNA was cut with Bam, H1, Sst1, EcoR1 and Bst1, electrophoresed, blotted, and hybridised to pMB22 and its subclones pMB22/S4 and pMB22/S12. In each case approximately 8 strongly hybridising bands were obtained. When this procedure was repeated using the restriction endonucleases Alu1, Ava1, Pst1 PvuII and Pvu1, approximately 16 strongly hybridising bands were seen with pMB22 and its subclone S4, while a subset of only 8 of these bands hybridised to the subclone of pMB22, S12. Digestion of *M. paratuberculosis* genomic DNA with Hinf1 produced 2 bands hybridising strongly with pMB22 and pMB22/S4, only one of which also hybridised with pMB22/S12. pMB22 and its subclones S4 and S12 were then used to probe Southern blots of Bam H1 restricted genomic DNA obtained from two laboratory strains of *M. avium* serotype 2 (Caddigg 16741) and serotype 5 (25546-759) [7]. A single band was found with both *M. avium* strains using pMB22 probe. pMB22/S12 did not hybridise to *M. avium* serotype 2 DNA, and pMB22/S4 hybridised only very weakly to a single band.

These results, taken together with those in example 5, indicate that pMB22 contains a sequence that is present in approximately 8 copies dispersed in the genome of *M. paratuberculosis* but absent in *M. avium* serotype 2. The enzymes giving 8 hybridising bands must not cut the insertion sequence contained within clone pMB22 and each band therefore represents a different genomic location of the ISMY insertion elements. Enzymes such as PvuII cut the element once and therefore produce two fragments for each genomic copy. The sequence pMB22/S12 must be derived from one of the PVu II fragments, whereas pMB22/S4 spans the PvuII site. The enzyme Hinf 1 must have at least 3 sites within the insertion element, and therefore each genomic copy of ISMY is cleaved to give the same two internal ISMY fragments, plus heterogenous ISMY fragments containing flanking DNA. A detailed restriction endonuclease map of pMB22 was derived and is shown (FIG. 3A).

The date presented show that the *M. paratuberculosis* and *M. avium* complex strains tested are very closely related, exhibiting less than 1% DNA base substitution between the two species [7,8]. However, the identical nature to *M. paratuberculosis* strains isolated from a wide variety of geographical sources and disease hosts, suggests that *M. paratuberculosis* is a conserved specific pathogen causing Johne's disease in cattle, goats, and at least one species of primate, and possibly causing some cases of Crohn's disease in humans. This would suggest there are specific genetic changes that characterise *M. paratuberculosis,* confering pathogenicity and enabling it to cause these diseases. The tight segregation of ISMY-1 insertion sequences to *M. paratuberculosis* and the specific absence of ISMY-1 from most laboratory strains of *M. avium* examined, would make ISMY-1 a strong candidate sequence responsible for the genetic changes in *M. paratuberculosis* endowing its pathogenicity.

Figure 3B:
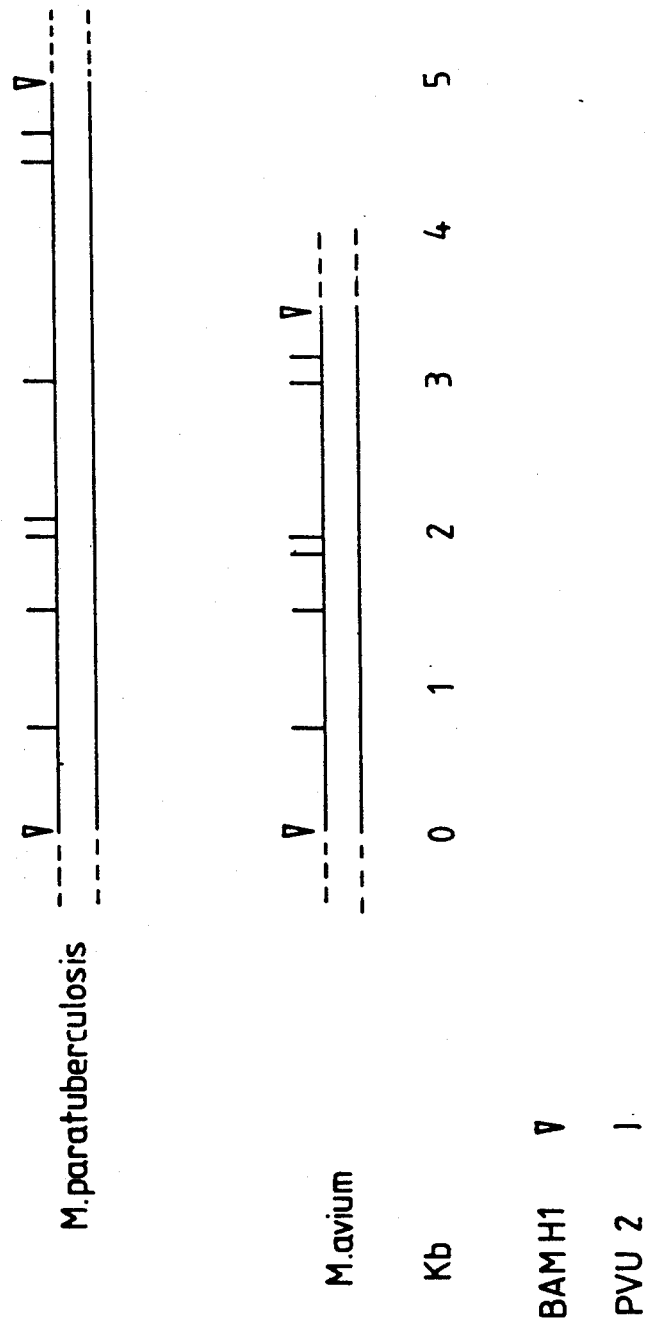

The organisation of genomic DNA flanking the insertion sequence ISMY-1 of the invention, identified within clone pMB22 and *M. paratuberculosis,* was examined with pMB22 and subclones, S4, S8 and S12 and the results compared with similar studies on *M. avium* genomic DNA. The maps are shown (FIG. 3B). Genomic DNA flanking ISMY-1 in pMB22 showed no changes detectable between *M. avium* and *M. paratuberculosis,* indicating a similar level of base substitution between DNA in this region as elsewhere in the genome. Since *M. paratuberculosis* and *M. avium* are evolutionarily very close, the presence of the repetitive element ISMY-1 in *M. paratuberculosis* is compatible with ISMY-1 being recently acquired by *M. paratuberculosis* causing a divergence from *M. avium*. Alternatively the sequence ISMY-1 may have been deleted from *M. avium* during evolution causing its divergence from *M. paratuberculosis.* Since the latter proposal would require precise excision and deletion of each copy of ISMY-1 from the *M. paratuberculosis* genome, an extremely unlikely event, the former explanation is more plausible. The repetitive sequence ISMY-1 would form an example of the genetic elements known as Insertion Sequences [12]. The DNA sequence of ISMY-1 was determined by single-stranded M13 sequencing and the partial sequence is shown (FIG. 4).

EXAMPLE 7

ISM related sequences in other mycobacteria

This section demonstrates the presence of sequences in other pathogenic mycobacteria which are related to ISMY-1 by sharing homology, and which are identified by hybridisation with pMB22 or its subclones under appropriate experimental conditions. As with ISMY-1, other members of the ISM family appear to confer pathogenicity on the mycobacterial host.

DNA from a collection of mycobactin-dependent *M. avium* strains isolated from diseases in wood-pigeon, deer, goat, pig and armadillo and also *M. avium* serotype 2 and *M. paratuberculosis* were hybridised with pMB22 and its subclones. Hybridisation of mycobactin-dependent *M. avium* strains with pMB22 gave banding patterns similar to those obtained with DNA from *M. avium* serotype 2, but also showed a series of additional bands, not present in *M. avium* serotype 2 (FIG. 5A). When washed at high stringency the signal from most of these additional bands was selectively removed. When representative DNA samples were probed with subclone pMB22/S4, these additional bands hybridised strongly, but only one faint band was obtained with *M. avium* serotype 2, derived from flanking DNA (FIG. 5B). The subclone pMB22/S12 hybridised ISMY-1 in *M. paratuberculosis* DNA but only to a single band in samples 157R and 157S. armadillo-derived mycobactin-dependent strains (FIG. 5C). The non-mycobactin dependent armadillo-derived strain of *M. paratuberculosis* 10911 did not hybridise either to pMB22/S4 or pMB22/S12. When these DNA samples were probed with an unrelated *M. paratuberculosis* DNA probe, very similar or identical banding patterns were obtained from all strains.

These results indicate that pathogenic mycobactin-dependent strains of *M. avium* contain insertion sequences related to ISMY-1 in the pathogen *M. paratuberculosis.* The strains 157R and 157S contain an insertion sequence closely related to ISMY-1 since it hybridised to both pMB22/S4 and pMB22/S12. The insertion sequence present in the deer, goat, wood pigeon and porcine mycobacterial isolates are less closely related to ISMY-1 and do not contain sequences homologous to pMB22/S12. The banding patterns were similar for some of the different strains in this group and the insertion sequence in these strains has been designated ISMY-2.

Further unselected *M. avium* strains were investigated for the presence of insertion sequences of the ISMY family. Several strains were found to contain copies of ISMY-2 or related insertion sequences, but to date no other mycobacterial strains containing ISMY-1 have been identified. Two further pathogens have been found to contain ISMY-related insertion sequences. DNA from the leprosy bacillus *M. leprae* contains a sequence that hybridised to pMB22/S4. DNA from the rat leprosy bacillus *Mycobacterium lepraemurium* contained a sequence that hybridised to pMB22/S4, but not to pMB22/S12.

These results show that insertion sequences related to ISMY-1 are found in a number of mycobacterial pathogens particularly within the *M. avium* complex including those isolated from AIDS patients. We have screened more than 20 further mainly saprophytic and environmental mycobacterial species and strains and found none to contain insertion sequences of the ISMY family. ISMY appears to segregate with mycobacterial pathogenicity.

APPLICATIONS AND USES OF THE INVENTION

Cloned DNA probes of the invention from recombinant DNA libraries derived from specific mycobacteria or synthetic DNA sequences based on information from such libraries and selected for mycobacterial strain or phenotypic specificity, are used in the specific identification of mycobacterial DNA or RNA and the differentiation of mycobacterial from other microbial sequences. Such specific mycobacterial DNA probes are also used for the precise differentiation between mycobacterial strains and species and the recognition or prediction of phenotypic properties such as drug sensitivity and pathogenicity.

In addition, DNA or RNA probes or synthetic oligonucleotides derived from all or part of the sequence ISMY-1 (in pMB22 deposited with NCIB No. 12461), ISMY-2, and other members of the ISMY family of mycobacterial insertion sequences of the invention sharing partial homology with ISMY-1, are used as probes for the specific detection of potentially pathogenic strains of mycobacteria. These include *M. paratuberculosis*, pathogenic forms of *M. avium* including those involved in AIDS superinfections, and other pathogenic mycobacteria contains ISMY sequences including *M. leprae*.

Precise identification and differentiation of mycobacteria as well as the specific detection of ISMY-containing pathogenic strains, is applied to environmental samples such as water, animal and human food stuffs, and soil. Such applications are useful in the prevention and public health containment of mycobacterial diseases in humans and animals. Tests using the methods and probes of the invention are also applied to medical and veterinary samples of tissue, tissue extracts, body fluids, including milk, and excreta, as well as to the accelerated identification and characterisation of mycobacteria grown in in-vitro cultures, and to the improvement of such culture conditions. These applications are useful in the diagnosis of mycobacterial diseases such as Johne's disease in cattle and other animals, mycobacterial diseases in zoo animals and birds, human mycobacterial diseases such as leprosy, *M. avium* infections, AIDS mycobacterial superinfections, and to human Crohn's disease.

In methods used in the tests, DNA probes are single or double-stranded or are RNA transcripts, and may be unlabelled or labelled with radioactive, biotinyl, fluorescent, enzyme immunological or other revealing agents or methods. Probes representing all or part of ISMY are used in solution phase systems or bound to solid phase supports such as cellulose, nylon, nitrocellulose, plastic, or gel systems, in the form of beads, tubes, or other matrix. Samples are treated to release mycobacterial DNA or RNA. Mechanical disruption, and/or sonication and/or enzymic treatments and/or heat treatment, and/or chemical treatments are used. Treated samples are mixed with the probe (boiled, if double-stranded) in a solution designed to allow hybridisation and prevent nuclease action. Hybridisation of specific probes to target DNA or RNA present in the sample is achieved by standard procedures.

Detection of hybrids is by a number of methods. Hydroxyapatite (HAP) may be added to bind double-stranded DNA or RNA, and the HAP is then washed to remove unhybridised probe. Other solid matrixes are used to bind hybrid. Alternatively, unhybridised probe is removed by digestion with single-strand specific nuclease followed by precipitation of hybrid by trichloroacetic acid, ethanol or other substance. Hybrids are detected by methods dependent on the revealing method used. Unlabelled probe DNA is bound to a solid matrix and used to hybridise to the sample. Target mycobacterial DNA or RNA homologous to the probe sequence becomes bound to the matrix via the probe. The matrix is washed and target DNA or RNA released by heating or transfer to denaturing solution. The target DNA or RNA is then detected directly by the methods described above. Alternatively the DNA or RNA is first amplified by polymerase chain reactions (PCR [12]) using DNA polymerase or reverse transcriptase plus DNA polymerase together with specific oligonucleotide primers for sequences present in the probe or ISMY sequence, and such primers form further aspects of the present invention. After amplification, target sequences are detected by any of the methods described above. Detection may involve differentiation between unreacted primers and primers that have been extended in the PCR reactions. In this case the primers are labelled and detection is dependent on the label used. Hybridisation of probe to unamplified or amplified target mycobacterial sequences is by standard procedures and dot blot methods or the identification of RFLPs are also used.

All or part of the mycobacterial insertion sequences of the invention including ISMY-1 (in pMB22), ISMY-2 and other members of the ISMY family sharing partial sequence homology with ISMY-1, are used to generate recombinant proteins or peptides or synthetic peptides based on ISMY sequences and such derived sequences, form further aspects of the present invention. Also of use are proteins mutated or altered in expression by ISMY.

Recombinant proteins and ISMY derived peptides are also used in immuno and other diagnostic assays using standard techniques applicable to medical, veterinary, environmental and in-vitro culture samples for the specific detection of ISMY-containing pathogenic mycobacteria. Antibodies to ISMY derived proteins or peptides whether polyclonal or monoclonal for use in such diagnostic immunoassays or other systems form further aspects of the present invention. Recombinant proteins based on ISMY sequences are used with or without computer-based structural studies for the rational design of specific drugs to modify or block their biological actions. Recombinant ISMY proteins or peptides may themselves be used as therapeutic agents to mediate specific biological effects in vivo such as immunomodulation.

All or part of the DNA sequence of members of the ISMY family may be used to engineer mutant bacteria or viruses and such mutant forms containing ISMY sequences form further aspects of the present invention. These are employed as specific vaccines for the prevention of diseases caused by pathogenic mycobacteria in medical and veterinary practise. They may also be used as agents in immunotherapy or diagnostics. Proteins or peptides derived from ISMY are also used as vaccines for the same purpose.

REFERENCES

1. Goodfellow M and Wayne LG. (1982). in The Biology of Mycobacteria. ed. Ratledge & Stanford. Academic Press. London.
2. Graham, DY, et al. (1987). Gastroenterol 92: 436–442.
3. Chiodini Rj, et al., (1984). The Cornell Veterinarian 74: 218–262.
4. Collins F. Int.J.Leprosy 54: 458–474.
5. Van Eden et al. (1988). Nature 331: 171–173.
6. Chiodini RJ et al. (1984). Dig.Dis.Sci. 29: 1073–1079.
7. McFadden JJ. et al. (1987) J.Clin.Microbiol. 25: 796–801.

8. McFadden JJ. et al. (1987). Mol.Microbiol. 1: 283-291.
9. Collins J, et al. (1987). Gastroenterol. 92: 1352.
10. Martin CM, et al (1987). Am.Rev.Res.Dis. 136: 344-348.
11. McClure HM, et al. (1987). J.Inf.Dis. 155: 1011-1019.
12. Cullum J. (1985). in Genetics of Bacteria. ed.Scaife J. et al., Academic Press, London.
13. Scharf SJ, et al. (1987). Science. 233: 1076-78.

We claim:

1. ISM-1 optionally carrying a revealing label.

2. A method for detecting the presence or absence of a mycobacterial strain or phenotype in a test sample, said method comprising:
   a) hybridizing a probe with a putative target nucleic acid sequence in said test sample,
      wherein said probe comprises a nucleic acid sequence having at least 70% homology with any contiguous nucleotide sequence of at least 20 nucleotides within an ISMY-1 sequence which is substantially equivalent to the DNA sequence of FIGS. 4 or 6, optionally said nucleic acid probe sequence combined with a revealing label; and
   b) detecting the presence or absence of said target nucleic acid sequence,
      thereby detecting the presence or absence of a mycobacterial strain or phenotype in said test sample.

3. The method of claim 2 wherein said ISMY-1 sequence is the sequence of FIG. 6.

4. A method according to claim 2 for the precise identification and differentiation of closely related mycobacterial strains and species.

5. A method according to claim 2 wherein one of the mycobacterial strain(s) is *M. paratuberculosis*.

6. A method according to claim 2 wherein one of the mycobacterial strain(s) is of the group *M. avium-intracellulare* or *M. avium* complex.

7. A method according to claim 2 wherein one of the mycobacterial strain(s) is *M. leprae*.

8. A method according to claim 2 wherein one of the mycobacteria cause AIDS superinfections or atypical tuberculosis.

9. A method according to claim 2 wherein the phenotype is pathogenicity or drug resistance.

10. A method according to claim 2 wherein the mycobacterial strain causes Johne's disease in animals or Crohn's disease in humans.

11. A method according to claim 2 wherein the sample comprises body fluids, tissue, tissue extracts, excreta, in vitro cultures, or environmental samples.

12. An isolated nucleotide sequence having at least 70% sequence homology with any contiguous sequence of at least 20 nucleotides of ISMY-1 of mycobacterial origin having the sequence of FIG. 4 or FIG. 6.

13. The isolated nucleotide sequence according to claim 12 where said ISMY-1 sequence is the sequence of FIG. 6.

14. An isolated nucleotide sequence having at least 70% sequence homology with any contiguous sequence of at least 20 nucleotides of ISMY-1 of mycobacterial origin having a sequence starting at nucleotide number 837 on contig 1 and terminating at nucleotide number 1037 on contig 2 in the sequence of FIG. 4.

15. The nucleotide sequence according to any of claims 12 to 14 carrying a revealing label.

16. A method of detecting the presence or absence of a mycobacterial strain or phenotype which comprises assaying a sample for mycobacterial DNA or RNA with a probe, said method comprising:
   a) hybridizing a probe with a putative target nucleic acid sequence in a test sample,
      wherein said probe comprises a nucleotide sequence having at least 70% sequence homology with mycobacterial origin having a sequence starting at nucleotide number 837 on contig 1 and terminating at nucleotide number 1037 on contig 2 in the sequence of FIG. 4, optionally said nucleic acid probe sequence combined with a revealing label; and
   b) detecting the presence or absence of said target nucleic acid sequence,
      thereby detecting the presence or absence of a mycobacterial strain or phenotype in said test sample.

17. A method of detecting the presence or absence or mycobacteria in a test sample, said method comprising:
   a) hybridizing a nucleotide sequence according to claim 12 with a putative target nucleic acid sequence in said test sample,
   b) conducting a polymerase chain reaction enzyme amplification method, and
   c) detecting the presence or absence or said target nucleic acid sequence in said test sample,
      thereby detecting the presence or absence of mycobacteria in said test sample.

18. The nucleotide sequence of claim 12, said sequence derived from the genome of a mycobacterium.

19. A method of detecting the presence or absence of mycobacteria in a test sample, said method comprising:
   (a) hybridizing a nucleotide sequence according to claim 13 with a putative target nucleic acid sequence in said test sample,
   (b) conducting a polymerase chain reaction enzyme amplification method, and
   (c) detecting the presence or absence of said target nucleic acid sequence in said test sample,
      thereby detecting the presence or absence of mycobacteria in said test sample.

20. A method for the detection of mycobacterial contamination of environmental, human or animal food samples comprising a method according to claim 19.

21. A method of detecting the presence or absence of mycobacteria in a test sample, said method comprising:
   (a) hybridizing a nucleotide sequence according to claim 14 with a putative target nucleic acid sequence in said test sample,
   (b) conducting a polymerase chain reaction enzyme amplification method, and
   (c) detecting the presence or absence of said target nucleic acid sequence in said test sample,
      thereby detecting the presence or absence or mycobacteria in said test sample.

22. An optionally labelled diagnostic reagent, optionally immobilised on a solid phase, said reagent consisting essentially of a DNA or RNA probe according to claim 12.

23. A method for diagnosing the presence or absence or Crohn's disease in humans or John's disease in animals said method comprising:
   a) contacting a sample from a human or animal body with a reagent according to claim 22, and
   b) detecting the presence or absence of a target nucleic acid sequence in said sample, thereby diagnosing the presence or absence or said disease.

24. An optionally labelled diagnostic reagent, optionally immobilized on a solid phase, said reagent consisting essentially of a nucleic acid sequence according to any one of claims 12 to 15.

25. A method for diagnosing the presence or absence or Crohn's disease in humans or John's disease in animals said method comprising:

(a) contacting a sample from a human or animal body with a reagent of claim 24, and b) detecting the presence or absence or a target nucleic acid sequence in said sample, thereby diagnosing the presence or absence of said disease.

26. A method for the detection of mycobacterial contamination of environmental, human or animal food samples comprising a method according to claim 24.

* * * * *

UNITED STATES PATENT AND TRADEMARK OFFICE
CERTIFICATE OF CORRECTION

PATENT NO. : 5,225,324
DATED : 6 July 1993
INVENTOR(S) : John-Jo McFadden and John Hermon-Taylor It is certified that error appears in the above-indentified patent and that said Letters Patent is hereby corrected as shown below:

Delete Drawing Sheets 5, 8, and 9, and substitute therefor the Drawing Sheets, consisting of FIGS. 4, 6-1, and 6-2, as shown on the attached pages.

Signed and Sealed this

Thirty-first Day of May, 1994

BRUCE LEHMAN

*Attest:*

*Attesting Officer*      *Commissioner of Patents and Trademarks*

Fig. 4.

CONTIG1

●CAGCTGGGTG ACGGCTTCCC ACACGTCGGG CACCTCGTCC AGCGGAACCC
ACACGCTGAG CCGCTGGGCC AGCATCGGGT TGGTGGACAG GCCGCCGCCC
ACCCACAGGT CCAGGCCGGG TCCGTGCTCG GGTGCTCGA CGCCGACGAA
CGCGACGTCG TGGGTCTCGT GCGAGACGTC CTGCAGGCCC GAGACCGCGG
TTTTGTACTT GCGCGGCAGG TTGGCGTATT CGGGGTTGTT CAGGGAGCGA
CGGACGATCT CCTCGATCGC GGGCGACGGA TCGAGCACCT CGTCGAGCGA
GTGCCGGCCA GCGGCGAGCC GTGGATGCCG CGCGGGCAGT CCGCGCAGGC
CTCGGTGGTC TGCAGCCCGA CGGACTCGAG CCGTCGCCAG ATCTCGGGCA
CGTCCTCGAT GCGAATCCAG TGCAGCTGCA GGTTTTCCCG GTCGCTGATA
TCGGCGGTGT CGCGGGCGAA TTCGGTGGAG ATCTGGCCGA GCGTGCGCAT
GGTGTGCGCC GACATCGCCT TGCCGTCGGA GCGGACCCGC ATCATGAAGT
ACTTGGCTTC GATCTTGTCG GTGTTGTCGT CACCGGTCCA GCTGCCGTCG
TAGCCCTGCT CGCGTTGGGT GTACAGGCCC ATCCACCGGA AGCGGCCGCG
CAGGTCGGAC TTGTCGATGC TGTCGAAACC CTGCTTGGCG TAGACGTTGA
TGATGCGCTC GCCGATCTGT TCAGCGGCCC GTCGGCCAGC TTGATCTTCT
CGGTGTCGTT GAGCGGTTCG CGATCTCCCA GCGCCCACTG ACCCTCGTTG
CGGGTCTTGA CGGGACGTGC GGTGGTCATG TGGTGTTCCT TACCTTTCTT
GAAGGGTGTT CGGGGCCGTC GCTTAGGCTT CGAATTGCCC AGGGACGTCG
GGTATGGCTT TCATGTGGTT GCTGTGTTGG ATGGCCAAG GAGATTGGCC
GCCCGCGGTC CCGCGACGAC TCGACCGCTA ATTGAGAGAT GCGATTGGAT
CGCTGTGTAA GGACACGTCG GCGTGGTCGT CTGCTGGGTT GATCTGGACA
ATGACGGTTA CGGAGGTGGT TGTGGCACAA CCTGTCTGGG CGGGCGTGGA
CGCCGGTAAG GCCGACCATT ACTGCATGGT TATTAACGAC GACGCGCAGC
GATTGCTCTC GCAGCGGGTG GCCAACGACG AGGCCGCGCT GCTGGAGTTG
ATTGCGGCGG TGACGACGTT GGCCGATGGA GGCGAGGT▶

Fig. 4 (continued)

CONTIG 2

```
•GATCGACCTC AACGCCGGCG CGCCGCGTTG CTGATCGCCT TGCTCATCGC
TGCCGGGCAG CGGCTGCTTT ATATTCCCGG GCGCACGGTC CATCAGCCGC
GGGTAGTTAC CGCGGCGAAG GCAAGACCGA CGCCAAAGAC GCTGCGATCA
TCGCCGATCA GGCCCGGATG CGCCACGACT TGCAGCCTCT GCGCGCCGGC
GATGACATCG CAGTCGAGCT GCGCATCCTG ACCAGCCGAC GTTCCGATCT
GGTGGCTGAT CGGACCCGGG CGATCGAACC GAATGCGCGC CCAGCTGCTG
GAATACTTTC GGCGCTGGAA CGCGCCTTCG ACTACAACAA GAGCCGTGCC
GCGCTGATCC TGCTTACTGG CTACCAAACT CCCGACGCGC TGCGAGCGCG
GCCAGGTGGC GCTCGAGTAG CCGCGTTCTT GCGTAAACGA AGGCCCGCAA
CGCCGATACC GTCGCAGCCA CCGCGCTGCA GGCCGCTAAC GCCCAACACA
GCATCGTGCC CGGCCAACAA CTGGCGGCCA CTGTGGTGGC CCGCCTGGCC
AAGGAGGTGA TGGCCCTCGA CACCGAAATC GGCGACACCG ACGCGATGAT
CGAGGAGCGA TTTCGCCGCC ACCGCCACGC CGAAATCATC CTGAGCATGC
CCGGATTCGG CGTCATCCTG GGCGCTGAGT TCCTCGCCGC CACCGGCGGG
GACATGGCCG CATTCGCCTC CGCCGACCGC CTCGCCGGTC GCGGCCTGGC
GCCGGTACCA CGAGATTCCG GCCGCATCAG CGGAAACCTC AAACGCCCCC
GACGCTACGA CCGGCGCCTG CTGCGCGCCT GCTACCTGTC GGCCTTGGTC
AGCATCCGCA CCGACCCCTC CTCGCGCACC TACTACGACC GAAAACGCAC
CGAAGGAAAA CGCCACACCC AAGCCGTCCT CGCCCTGGCC CGCCGCCGCC
TCAACGTCCT GTGGGCCATG CTGCGCGACC ACGCTGTCTA CCACCCCGCA
ACCACTACCG CGGCGGCTTG ACAACGTCAT TGAGAATCTC CTTCGCGAAC
ATTCCCCGGT GTGCGACGCA CCGGGGTGGT GTTCCTGACG GCGGCTCAGA
TCGGCCTGCT ACGGGGCCGG GATGGGCTGT CGGCCGCGGC ATCGCGATGA
TGTTGGGGCT TTAGGCACCC GCAAGTTCGT CGTTGGACCC ACGGGTCGCG
ATTCCCATAG TGCACTACTT GCGGCCGCGT CAGTAGAGGT CGCATGTTGT
GAGGGCACAA CCGGACGTTG TGTGCGCCGC TTCACGATGG GTGACGGCGA
TCACTTTGCG GGCCAGGCGA ATTGCCGGGC CGGTCGCTGC CGTGAGGTTG
GCAATTCCGG CCTGATTGGC AACCTTGGTC AGGCCGGGCG TCAGACCGAA
TCCCGTGGCG GAACGTCCGT TCTGCGGCCC CCGAGTTGGG CCGGCAGCCG
GGTGTATCCG TGCAAGTTGA TCAGCGACCG CCGTTGCGGG CGCGT▶
```

Patent No. 5,225,324

```
TCCTTACCTTTCTTGAAGGGTGTTCGGGGCCGTCGCTTAGGCTTCGAATTGCCCAGGGAC
     10        20        30        40        50        60

GTCGGGTATGGCTTTCATGTGGTTGCTGTGTTGGATGGCCGAAGGAGATTGGCCGCCCGC
     70        80        90       100       110       120

GGTCCCGCGACGACTCGACCGCTAATTGAGAGATGCGATTGGATCGCTGTGTAAGGACAC
    130       140       150       160       170       180
                                           SD          V
GTCGGCGTGGTCGTCTGCTGGGTTGATCTGGACAATGACGGTTACGGAGGTGGTTGTGGC
    190       200       210       220       230       240

A  Q  P  V  W  A  G  V  D  A  G  K  A  D  H  Y  C  M  V  I
ACAACCTGTCTGGGCGGGCGTGGACGCCGGTAAGGCCGACCATTACTGCATGGTTATTAA
    250       260       270       280       290       300

N  D  D  A  Q  R  L  L  S  Q  R  V  A  N  D  E  A  A  L  L
CGACGACGCGCAGCGATTGCTCTCGCAGCGGGTGGCCAACGACGAGGCCGCGCTGCTGGA
    310       320       330       340       350       360

E  L  I  A  A  V  T  T  L  A  D  G  G  E  V  T  W  A  I  D
GTTGATTGCGGCGGTGACGACGTTGGCCGATGGAGGCGAGGTCACGTGGGCGATCGACCT
    370       380       390       400       410       420

L  N  A  G  G  A  A  L  L  I  A  L  L  I  A  A  G  Q  R  L
CAACGCCGGCGGCGCCGCGTTGCTGATCGCCTTGCTCATCGCTGCCGGGCAGCGGCTGCT
    430       440       450       460       470       480

L  Y  I  P  G  R  T  V  H  H  A  A  G  S  Y  R  G  E  G  K
TTATATTCCCGGCGCACGGTCCATCACGCCGCGGGTAGTTACCGCGGCGAAGGCAAGAC
    490       500       510       520       530       540

T  D  A  K  D  A  A  I  I  A  D  Q  A  R  M  R  H  D  L  Q
CGACGCCAAAGACGCTGCGATCATCGCCGATCAGGCCCGGATGCGCCACGACTTGCAGCC
    550       560       570       580       590       600

P  L  R  A  G  D  D  I  A  V  E  L  R  I  L  T  S  R  R  S
TCTGCGCGCCGGCGATGACATCGCAGTCGAGCTGCGCATCCTGACCAGCCGACGTTCCGA
    610       620       630       640       650       660

D  L  V  A  D  R  T  R  A  I  E  P  N  A  R  P  A  A  G  I
TCTGGTGGCTGATCGGACCCGGGCGATCGAACCGAATGCGCGCCCAGCTGCTGGAATACT
    670       680       690       700       710       720

L  S  A  L  E  R  A  F  D  Y  N  K  S  R  A  A  L  I  L  L
TTCGGCGCTGGAACGCGCCTTCGACTACAACAAGAGCCGTGCCGCGCTGATCCTGCTTAC
    730       740       750       760       770       780
```

FIG. 6-1

```
T  G  Y  Q  T  P  D  A  L  R  S  A  G  G  A  R  V  A  A  F
TGGCTACCAAACTCCCGACGCGCTGCGCAGCGCCGGTGGCGCTCGAGTAGCCGCGTTCTT
         790       800       810       820       830       840

L  R  K  R  K  A  R  N  A  D  T  V  A  A  T  A  L  Q  A  A
GCGTAAACGCAAGGCCCGCAACGCCGATACCGTCGCAGCCACCGCGCTGCAGGCCGCTAA
         850       860       870       880       890       900

N  A  Q  H  S  I  V  P  G  Q  Q  L  A  A  T  V  V  A  R  L
CGCCCAACACAGCATCGTGCCCGGCCAACAACTGGCGGCCACTGTGGTGGCCCGCCTGGC
         910       920       930       940       950       960

A  K  E  V  M  A  L  D  T  E  I  G  D  T  D  A  M  I  E  E
CAAGGAGGTGATGGCCCTCGACACCGAAATCGGCGACACCGACGCGATGATCGAGGAGCG
         970       980       990       1000      1010      1020

R  F  R  R  H  R  H  A  E  I  I  L  S  M  P  G  F  V  I
ATTTCGCCGCCACCGCCACGCCGAAATCATCCTGAGCATGCCCGGATTCGGCGTCATCCT
         1030      1040      1050      1060      1070      1080

L  G  A  E  F  L  A  A  T  G  G  D  M  A  A  F  A  S  A  D
GGGCGCTGAGTTCCTCGCCGCCACCGGCGGGGACATGGCCGCATTCGCCTCCGCCGACCG
         1090      1100      1110      1120      1130      1140

R  L  A  G  V  A  G  L  A  P  V  P  R  D  S  G  R  I  S  G
CCTCGCCGGCGTCGCCGGCCTGGCGCCGGTACCACGAGATTCCGGCCGCATCAGCGGAAA
         1150      1160      1170      1180      1190      1200

N  L  K  R  P  R  R  Y  D  R  R  L  L  R  A  C  Y  L  S  A
CCTCAAACGCCCCCGACGCTACGACCGGCGCCTGCTGCGCGCCTGCTACCTGTCGGCCTT
         1210      1220      1230      1240      1250      1260

L  V  S  I  R  T  D  P  S  S  R  T  Y  Y  D  R  K  R  T  E
GGTCAGCATCCGCACCGACCCCTCCTCGCGCACCTACTACGACCGAAAAACGCACCGAAGG
         1270      1280      1290      1300      1310      1320

G  K  R  H  T  Q  A  V  L  A  L  A  R  R  R  L  N  V  L  W
AAAACGCCACACCCAAGCCGTCCTCGCCCTGGCCCGCCGCCGCCTCAACGTCCTGTGGGC
         1330      1340      1350      1360      1370      1380

A  M  L  R  D  H  A  V  Y  H  P  A  T  T  T  A  A  A
CATGCTGCGCGACCACGCTGTCTACCACCCCGCAACCACTACCGCGGCGGCTTGACAACG
         1390      1400      1410      1420      1430      1440

TCATTGAGAAT
    1450
```

FIG. 6-2